United States Patent [19]

Nicholson

[11] 4,263,900
[45] Apr. 28, 1981

[54] PRESSURE-RESPONSIVE SURGICAL TOOL ASSEMBLY

[75] Inventor: James E. Nicholson, Lincoln, Mass.

[73] Assignee: Codman and Shurtleff, Inc., Randolph, Mass.

[21] Appl. No.: 31,720

[22] Filed: Apr. 20, 1979

[51] Int. Cl.³ .............................................. A61B 17/02
[52] U.S. Cl. .................................. 128/20; 128/303 R
[58] Field of Search ..................... 128/15, 16, 20, 748, 128/344, 303 R

[56] References Cited

U.S. PATENT DOCUMENTS

| 3,649,948 | 3/1972 | Porter | 339/16 R |
|---|---|---|---|
| 3,882,855 | 5/1975 | Schulte et al. | 128/20 |
| 3,888,117 | 7/1975 | Lewis | 128/20 X |
| 4,080,653 | 3/1978 | Barnes, Jr. et al. | 128/748 X |
| 4,114,606 | 9/1978 | Seylar | 128/748 X |

Primary Examiner—Robert W. Michell
Assistant Examiner—Michael H. Thaler
Attorney, Agent, or Firm—Donal N. Tobin

[57] ABSTRACT

A pressure-responsive surgical tool assembly includes an inflatable enclosure and a pair of electrodes positioned therein. The electrodes are adapted to contact each other and operatively move away from each other under an increase of fluid pressure inside the enclosure until electrical contact is broken. An electrical lead is connected to each electrode for electrically monitoring the condition of electrode contact. A flexible tubing is connected to the enclosure to provide fluid flow therein to increase the pressure inside. A surgical tool overlies at least one of the electrodes and is adapted to transmit force applied from it to that associated electrode. Application of force by the tool initially causes the electrodes to contact each other and to remain in contact until the pressure inside the enclosure substantially balances the applied pressure from the tool whereupon electrode contact is broken.

11 Claims, 10 Drawing Figures

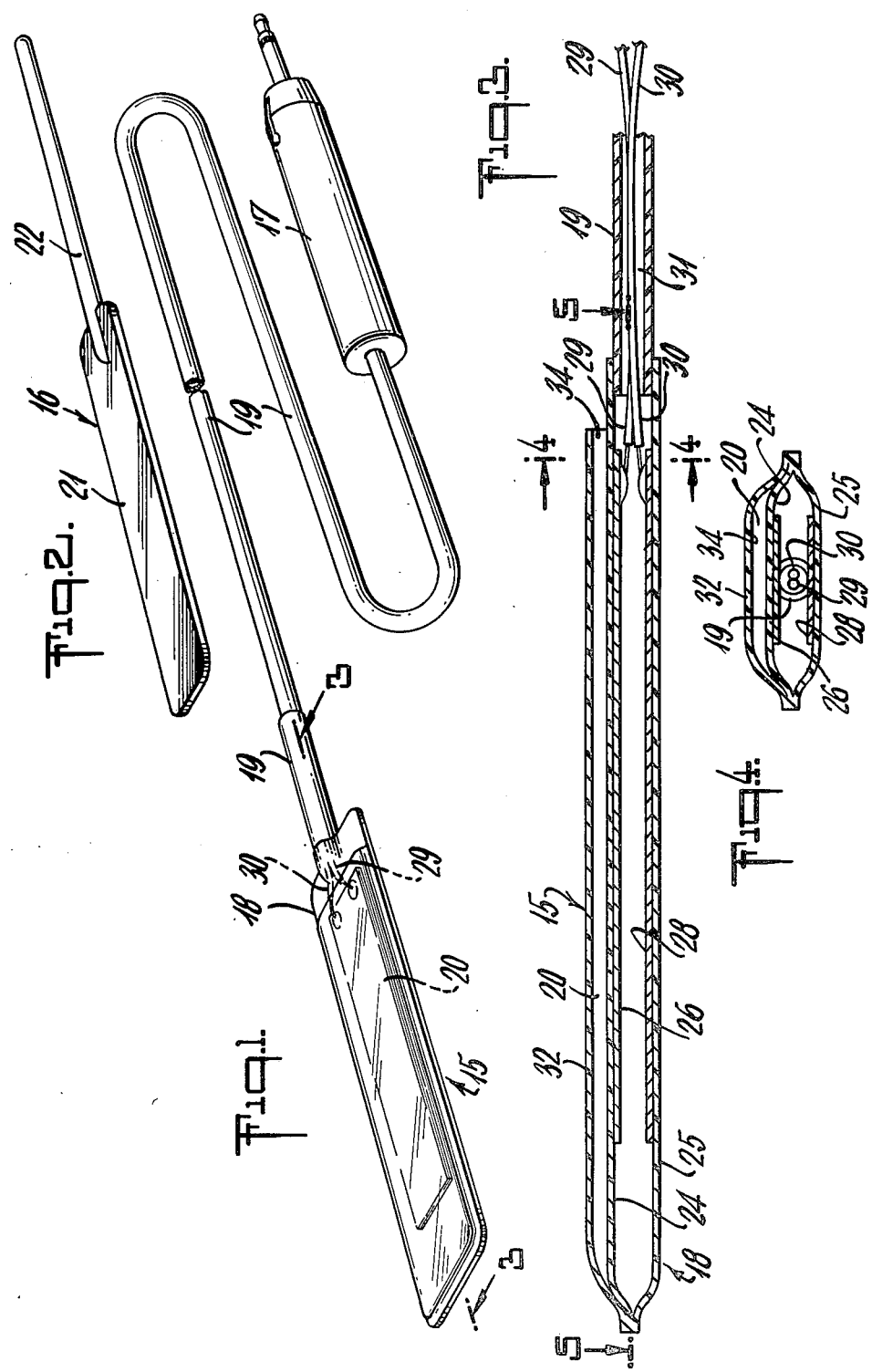

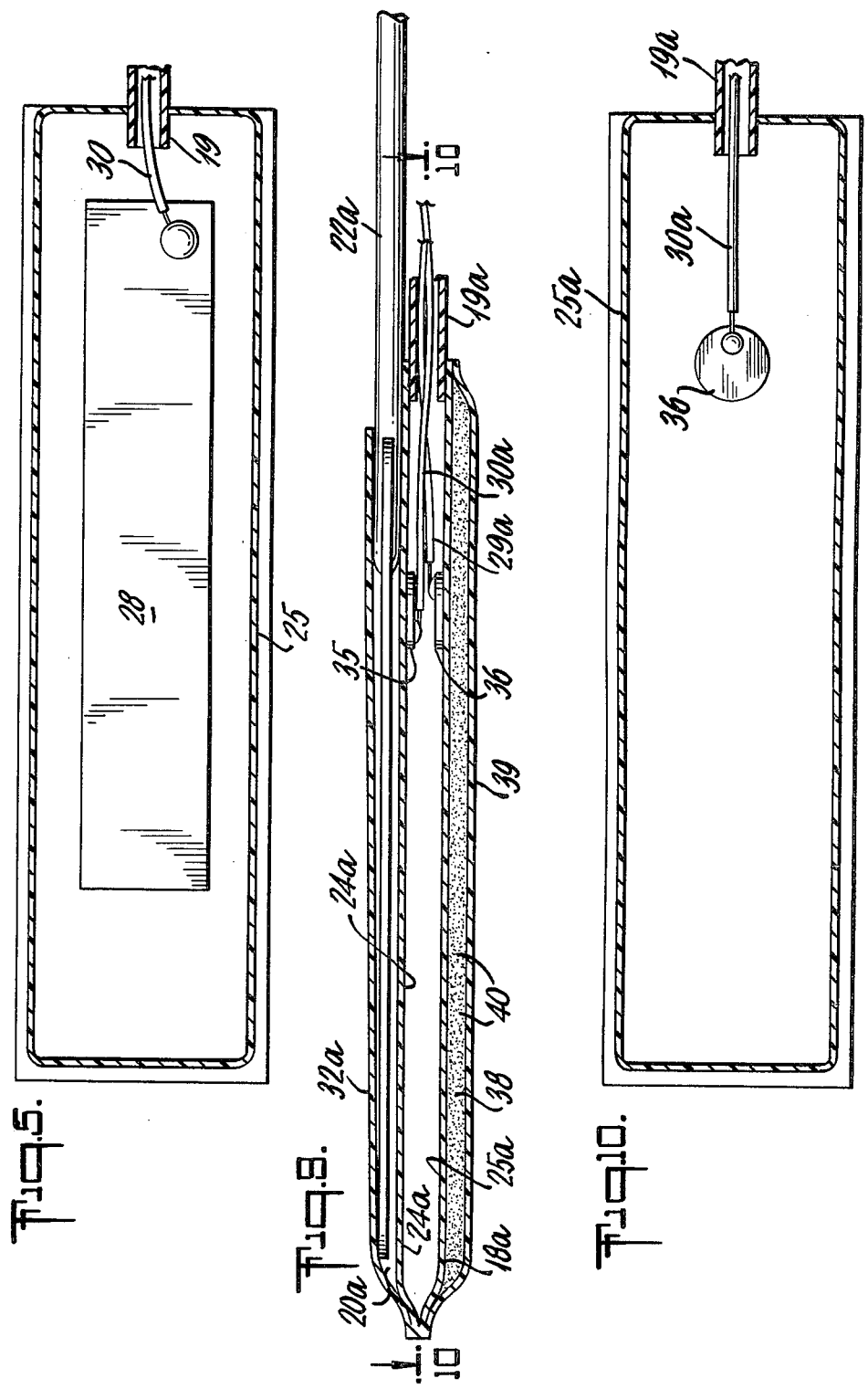

U.S. Patent    Apr. 28, 1981    Sheet 3 of 3    4,263,900
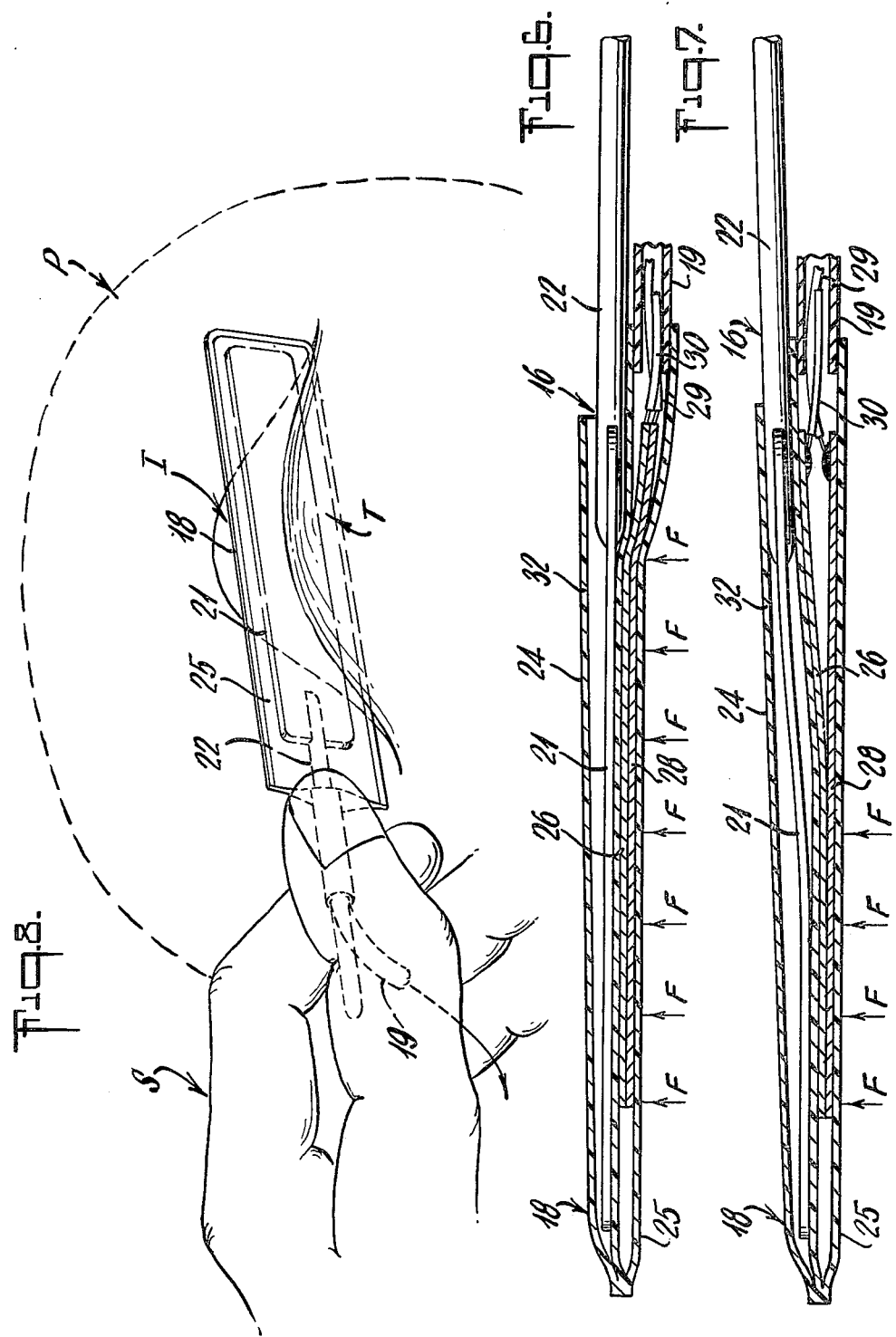

PRESSURE-RESPONSIVE SURGICAL TOOL ASSEMBLY

BACKGROUND OF THE INVENTION

The present invention relates to a pressure-responsive surgical tool assembly, and more particularly, concerns a surgical retractor tool which provides an indication of the pressure being applied by the retractor against tissue or the like during surgery.

During surgical operations, a retractor is employed to expose the area on which the operation is contemplated; the retractor's purpose is to separate the edges of a surgical incision and then restrain the underlying tissues or organs from interfering with the operative process. Most retractors are hand-held by the surgeon who manipulates the retractor until the area to be worked on is properly exposed. Once the retractor is properly in position, it is often mounted in suitable framework in order to maintain that position and prevent the retractor from inadvertent movement.

Use of a retraction instrument during surgery of course necessitates caution when pressing the retractor blade against tissue, an organ or the like; extreme care is taken so that damage to the retracted item may be avoided. In most cases, the surgeon can visualize the retracted tissue clearly enough to determine that the retractive movements are not causing any harm to the patient. However, there are instances during surgery when the manipulation of the retractor may be causing damage to the tissue or organ unbeknownst to the surgeon due to the delicacy of the organ or lack of sufficient feedback data to indicate to the surgeon that excessive pressure by the retractor is occurring. These conditions arise, for example, during brain surgery wherein the retractor is utilized to hold back sections of the dura covering the brain or even portions of the brain itself. Inasmuch as the brain is very sensitive to application of pressure, use of the retractor in this area of the body could cause problems if not closely monitored. For instance, excessive pressure against the brain during craniotomies by a brain retractor have been known to cause significant edema in the area corresponding to retractor blade location. Excessive pressure by the brain retractor for protracted periods could even cause functional neurobiological changes in the patient. One reason for undue application of excessive pressure by the brain retractor is that the amount of pressure of the hand-held retractor against the brain tissue is based purely on the skill and judgment of the surgeon. Another explanation is that retraction pressure is generally excessive when that pressure surpasses local venous pressure in vessels within the retracted area, such that local blood flow is restricted or occluded. The relationship of hand-held retraction pressure to venous pressure is virtually indeterminable without some means of measurement. The surgeon's experience, skill and understanding of the operation are factors which dictate the utilization of the brain retractor and the pressure which is applied thereby, including the length of time the retractor is applied. In other words, the surgeon who uses this commonly employed hand-held brain retractor has had no real, monitored indication of the amount of pressure which is being applied against the brain surface during this surgery. As a result, reliance upon the "feel" of the surgeon could cause inadvertently high pressure being applied which, in the long run, may restrict or occlude blood flow and actually cause serious defects in the brain's function. It can be seen that there is a real and serious need to provide the surgeon with a retraction device for brain surgery and other delicate surgical operations which will allow him to monitor or even regulate the amount of pressure being applied by the retraction device.

There have been other devices used to assist medical staff in acquiring data particularly about the brain. For example, it has been known to monitor intracranial pressure to quickly locate areas of elevated pressure which may stem from a variety of different causes. One such device, commonly referred to as the "Numoto" switch is described in U.S. Pat. No. 3,649,948. This Numoto-type switch is implanted within the skull of a patient to monitor intracranial pressure. The switch, which is generally flat and may be the size of a dime, consists of two contact electrodes sealed in a thin silicone rubber envelope and connected to an external manometer reservoir by a pneumatic tube. Pressure within the cranium is registered on the manometer. However, neither the Numoto-type switch described in the above patent nor other devices available to the surgeon have been employed in the sense of a retraction instrument in order to provide a surgeon with actual pressure data during the operation itself when the retraction instrument is being utilized to hold back tissue, organs, and sensitive areas of the body. Accordingly, in order to provide the surgeon with such a retraction device for indicating pressure levels applied by the retractor, the present invention is directed.

SUMMARY OF THE INVENTION

A pressure-responsive surgical tool assembly comprises an inflatable enclosure and a pair of electrodes positioned therein. These electrodes are adapted to contact each other and operatively move away from each other under an increase of fluid pressure inside the enclosure until the electrical contact is broken. An electrical lead is connected to each electrode for electrically monitoring the condition of electrode contact and noncontact. The assembly includes means for providing fluid flow into the enclosure for regulating the pressure inside same. In addition, means is provided for receiving a surgical tool which is adapted to overlie at least one of the electrodes and which is adapted to transmit force applied from it to that associated electrode. Application of force by the tool, against a tissue or like surface initially causes the electrodes to contact each other and to remain in contact until the pressure inside the enclosure substantially balances the applied pressure from the tool, whereupon the electrode contact is broken.

In the preferred embodiment of the present invention, the enclosure is a flexible housing adapted to expand when the volumes inside increases due to a pressure increase. Each electrode is attached to the interior surface of opposite, facing walls of the housing so that the operative movement of the electrodes is caused by the expanding walls of the housing when the pressure inside increases. This embodiment is adapted to be used with a standard retractor which commonly includes a retractor blade and a handle extending therefrom for grasping purposes by the surgeon. A pouch is connected to the assembly adjacent the housing into which the blade of the retractor is adapted to fit so that the retractor blade overlies one electrode. Long, rectangularly shaped electrodes, similar to the shape of the retractor blade, provides substantial distribution of force which is transmitted from the blade to the underlying electrode. In this structure, the entire electrode surface forms the sensitive retractor area.

In another embodiment of the present invention, the blade area of the retractor significantly exceeds the mating surface area of the underlying electrode. In order to transmit the force more effectively from blade to electrode, the surgical tool assembly includes a fluid-filled pocket overlying the other of the two electrodes so that the housing containing the electrodes is effectively sandwiched between the retractor blade pouch and the fluid-filled pocket.

In accordance with the principles of this invention, there is provided a surgical tool assembly which offers the advantage of providing the surgeon with an indication of the amount of pressure being applied by that tool during surgery. By providing an indication of applied pressure against a delicate tissue surface or the like, the surgeon can work within safe pressure levels such that tissue trauma may be avoided. In addition, the present invention is constructed to employ existing, standard retractor blades thereby minimizing change in standard operation procedures and equipment. Of course, the benefit to the patient offered by the present invention is paramount inasmuch as it presents a significant contribution to the surgeon in reducing the dangers which, up until now, stem from the un-monitored use of hand-held surgical retractors.

BRIEF DESCRIPTION OF THE DRAWINGS

FIG. 1 is a perspective view of the preferred pressure-responsive assembly for housing a surgical tool;

FIG. 2 is a perspective view of a typical retractor instrument, the blade of which slides into the pouch portion of the preferred housing assembly as illustrated in FIG. 1;

FIG. 3 is a cross-sectional view taken along line 3—3 of FIG. 1 illustrating the face to face aligning position of the electrodes within the housing of the assembly;

FIG. 4 is a cross-sectional view taken along line 4—4 of FIG. 1;

FIG. 5 is a cross-sectional view taken along line 5—5 of FIG. 1 illustrating the rectangular configurations of the housing and the electrode in this particular embodiment;

FIG. 6 is a cross-sectional view illustrating the embodiment of FIG. 3 with the electrodes in a complete surface to surface engaging contact;

FIG. 7 is a cross-sectional view of the embodiment illustrated in FIG. 3 with the electrodes only in partial contact due to the local application of force by the retractor blade.

FIG. 8 is a perspective view illustrating the surgical tool assembly in operation and being pressed against an edge of a typical incision during surgery;

FIG. 9 is a cross-sectional view of an alternate embodiment of the invention, illustrating the retractor instrument in position overlying one electrode, and a fluid-filled pocket overlying the other of the electrode for uniformity in force distribution by the blade during use; and FIG. 10 is a cross-sectional view taken along line 10—10 of FIG. 9 illustrating the small electrode attached to the interior surface of the housing wall.

DETAILED DESCRIPTION

While this invention is satisfied by embodiments in many different forms there is shown in the drawings and will herein be described in detail preferred embodiments of the invention, with the understanding that the present disclosure is to be considered as exemplary of the principles of the invention and is not intended to limit the invention to the embodiment or embodiments illustrated. The scope of the invention will be pointed out in the appended claims.

Adverting to the drawings, particularly FIGS. 1 and 2, there is illustrated a pressure-responsive device 15 which is particularly useful with a surgical tool such as a retractor 16. Pressure-responsive device 15 generally includes a flexible housing 18, a length of flexible tubing 19 connected to the housing for providing the flow of fluid to the housing and for enclosing the electrical leads which are connected to elements inside the housing, and a pouch 20 located adjacent housing 18 and adapted to receive the blade portion 21 of retractor 16. In addition to having a substantially flat blade, retractor 16 also includes a handle 22 attached to the blade and being sufficiently long to extend beyond the housing after the blade is slidably and snugly fit inside the housing pouch. Handle 22 thereby facilitates usage of the tool assembly by the operator. Tubing 19 terminates at connector 17 at its remote end to provide a connection for receiving both fluid and electrical energy from respective sources of supply.

Referring now to FIGS. 3-5, in conjunction with FIG. 1, the details of the pressure-responsive device are more clearly illustrated. In particular, housing 18, in this preferred embodiment, is generally rectangularly shaped and may be fabricated from two sheets of flexible, thermoplastic material, an upper sheet 24 and a lower sheet 25, which are sealed about their entire peripheries in order to form an enclosure. Both upper sheet 24 and lower sheet 25 have bonded to the surface which will form the interior wall of the closure an electrode, an upper electrode 26 and a lower electrode 28 on the respective upper and lower flexible sheets. These electrodes are shaped substantially similarly to the rectangular shape of each flexible sheet, as more clearly seen by briefly referring to FIG. 5 wherein bottom electrode 28 is illustrated on bottom sheet 25. It is preferable to utilize a thin electrically conductive material, or an electrically coated material for these electrodes. These thin electrodes in addition, will be flexible and provide the ability to conform to the configuration of the flexible sheet to which it is bonded. Bonding, of course, may be accomplished by cementing the electrode to the sheet or by other convenient techniques. Thus, when the flexible housing expands due to increase of pressure inside, the walls of the housing formed by the flexible sheets will tend to spread apart and move away from each other, carrying the attached electrode with it in the direction of expanse. This feature will be described in greater detail hereinafter. Accordingly, as seen especially in FIG. 5, electrode 28 is rectangularly shaped and covers a major portion of bottom sheet 25 which forms one of the walls of the housing of the device.

Inasmuch as each electrode serves to make an electrical contact with the other, an electrical lead is connected to each electrode, one lead 29 to upper electrode 26, another lead 30 connected to bottom electrode 28. The connection may be soldered, ultrasonically bonded or joined by other means to make the attachment between electrical lead and electrode.

When housing 18 is being fabricated, the length of flexible tubing 19 is positioned between an edge surface of both upper and lower flexible sheets, and is sealed to the housing when the peripheries of the sheets are sealed together. It is appreciated that the tubing may be sealed to one sheet beforehand as a pre-assembly operation. Thus, the lumen 31 of tubing 19 communicates with the interior of housing 18, and it is through lumen 31 which fluid pressure from a pressure source is allowed to enter the interior of the housing. Moreover, electrical leades 29 and 30 are slipped through lumen 31 during fabrication so that these leads are free to make an electrical contact at the remote end of the tubing (not shown). Accordingly, flexible tubing 19 serves the dual purpose of providing a medium for pneumatic purposes and for electrical purposes. Thus, connector 17 may be an electropneumatic connector such as described in the aforementioned U.S. Pat. No. 3,649,948, or other similar connector to adequately provide this dual electric and pneumatic role.

In order to retain retractor 16 in the appropriate position regarding pressure-responsive device 15, a pouch 20 is provided. This pouch is formed by a thin cover sheet 32, similar to flexible sheets 24 and 25. During fabrication, cover sheet 32 is also sealed around its entire periphery to housing 18, however, the edge 34 adjacent to the edge where tubing 19 is connected, is left open. In many instances, it is preferred to use a single sheet of flexible plastic material to form the housing and pouch. By folding the single sheet twice into a flat "S"-shaped structure, the lower and middle legs of the "S" serve as the upper and lower walls of the housing, while the upper leg of the "S" serves as the pouch cover. In this type fabrication, only the open peripheries need to be sealed together to join the edges for a completed closure as described. This then forms a pouch 20 adjacent housing 18 into which blade 21 of the retractor is adapted to slidably fit. It is preferred to make this pouch so that the blade will also fit snugly and tightly to reduce or eliminate any undesirable movement or play of the tool itself during use. The handle of the retractor extends out of the pouch and beyond the housing for easy grasping of the operator of this assembly.

It can therefore be seen that the completed housing assembly 18 is constructed so that upper electrode 26 and lower electrode 28 face each other in substantial alignment. The operation of this embodiment is illustrated in FIG. 6-8. A typical incision "I" made on patient "P" is schematically illustrated in FIG. 8. The retractor tool assembly of the present invention is assembled so that retractor blade 21 is fit inside the pouch adjacent flexible assembly 18, with handle 22 extending therefrom. The hand of surgeon "S" grasps handle 22 and applies the retractor tool against tissue "T" so that bottom sheet 25 is in direct contact with tissue "T", blade 21 being on the opposite side of the device. From this structural configuration, it is noted that blade 21 overlies upper electrode 26 in the embodiment being described, blade 21 and electrode 26 also being substantially similar in effective surface area. At this time, tubing 19 is connected to a fluid pressure source (not shown), while the electrical leads connected to the electrodes are also connected to this source in order to monitor the condition of electrode contact or non-contact. When the hand of surgeon "S" presses blade 21 in the direction of tissue "T" bottom sheet 25 comes in direct contact with the tissue to be moved or separated. Accordingly, the applied force of the blade is transmitted to the underlying electrode; since the internal pressure of the housing is at or near barometric pressure, the same as the environmental pressure, this applied force causes both upper electrode 26 and lower electrode 28 to make contact with each other, as more clearly seen in FIG. 6 where the force distribution "F" coming from the tissue is applied substantially uniformly. The contact of the electrodes serves as a closed switch, sending a signal to the controlled fluid pressure source to supply air or other fluid from a reservoir in the pressure source through tubing 19 and into housing 18. This increase of pressure inside housing 18 causes electrodes 26 and 28 to move away from each other as the walls of the enclosure expand. When the pressure inside the housing is equal to or slightly greater than the applied pressure by retractor blade 21, the electrodes are completely separated from each other and electrical contact is broken. At this time, the electrical switch is opened, thereby causing the air supply through the tubing to terminate. Accordingly, this pressure balance between externally applied pressure and internal pressure in the housing may be monitored to provide an indication to the surgeon of the level of pressure exerted against the tissue of the patient. Various fluid pressure sources may be utilized to provide such an indication such as those systems described in U.S. Pat. Nos. 3,649,948; 4,080,653 and 4,114,606, or other such devices. It is appreciated that blade 21 is substantially rigid so that sufficient force may be applied against the tissue in order to perform effectively the function of the retractor tool. It can also be seen that an increase in force applied by the blade against the tissue, once the electrical contact of the electrodes is broken, will cause the electrodes to come in contact once again, thereby closing the switch, the signalling for an increase in the flow of air into the housing. On the other hand, if the pressure inside housing 18 exceeds the applied pressure, pressure may be reduced within the housing by venting the air from the housing, thereby urging the electrodes once again to come in contact with each other and then indicate a lower pressure level on the monitor being used. Therefore, the pressure being applied, which usually varies over a given time frame, may be monitored even as these variations occur, depending upon the response time of the pressure source monitoring system.

In FIG. 7, a variation of applied force "F" is shown wherein the blade, because of angular application or due to irregularities in the tissue surface against which it is applied, is essentially applied locally to a certain area of the tissue next to the incision. When using the flexible electrode which is compatible with the flexible housing sheets, a local force will urge only a segment of the electrodes to contact each other, this segment being less than the entire surface area of each electrode. This, of course, still effectively produces electrical contact to provide the closed switching feature. In this instance, air will continue to enter into housing 18 until the last point of electrical contact is broken. Thus, it can be seen that this tool may be used to retract large areas of tissue, organs or the like, or even small surfaces where virtually point contact between tool and tissue is required.

A variation of the above-described embodiment is illustrated in FIGS. 9 and 10, wherein the surface of retractor blade 21a significantly exceeds the mating surface area of the underlying electrode 35. In this embodiment, upper electrode 35 on upper flexible sheet 24a and lower electrode 36 on lower flexible sheet 25a are substantially circular discs bonded to the respective interior surfaces of the housing walls. An electrical lead, such as lead 30a, is connected to each electrode to make an electrical contact. As can be seen when using electrodes of this type which are much smaller than the retractor blade, it is possible to have a force applied at the opposite end of the housing and, perhaps, not have the electrodes make electrical contact with each other. To overcome this problem, a pocket 38 is formed overlying electrode 36 on the opposite side of housing from pouch 20a. Another flexible sheet 39 is employed to form pocket 38 and, during fabrication, pocket 38 is sealed with a preferably incompressible fluid 40 inside the pocket. A saline solution or the like may be the fluid of choice. Thus, the electrodes are effectively sandwiched between the pouch and the fluid-filled pocket. This configuration assists in assuring that an electrical contact can be made by the electrodes even when the blade is applied against a tissue surface remote from the electrode surface. Thus, force from the blade may be transmitted to its underlying electrode from any point along the length of the blade to thereby cause the electrodes to make electrical contact.

While various materials may be employed to fabricate the present invention, the flexible housing sheets are preferably made of vinyl or other suitable thermoplastic material. Thin, light-weight material is normally chosen so as to not encumber the retractor during its normal use; also, in many instances, it is preferable to use a transparent material so that visual utilization of the retractor can be maintained. The electrodes are preferably formed of a thin, copper or gold-coated metallic strip, sufficiently pliant in nature so that they can conform to the flexible sheath as they expand with increased pressure. The retractor is preferably made of medical grade, malleable stainless steel or a comparable metal which may be typically used to make retractors. It can be appreciated that the size of the housing may vary according to the size of the retractor being used. Construction of the enclosure is such that approximately 1 mm. Hg. internal pressure will cause electrodes to separate and break electrical contact when the assembly is at rest in air at one atmosphere pressure.

Thus, the present invention provides a pressure-responsive surgical tool assembly which advantageously provides the user with the ability to monitor the amount of pressure which the tool applies against tissue, organs or the like during surgery, so that the surgeon will have knowledge immediately at hand during the operation of levels within which to work for purposes of safety to the patient.

I claim:

1. A pressure-responsive surgical retractor tool assembly comprising:
   an elongated inflatable enclosure having oppositely facing walls and having a distal end and having a proximal end;
   means near said proximal end of said elongated enclosure for providing fluid flow into said enclosure;
   a pair of thin electrode strips each fixed to its adjacent, oppositely facing wall and positioned within said enclosure in confronting relationship on said oppositely faced walls, each electrode strip extending axially along said elongated enclosure and terminating near said distal end;
   said electrode strips adapted to contact each other when said envelope is in the uninflated, collapsed position and adapted to peel apart as said elongated enclosure is inflated and to break electrical contact therebetween only when the entire surfaces of the electrodes separate thereby permitting said electrodes to indicate the maximum pressure to which any part of the electrode is exposed;
   an electrical lead connected to each electrode strip and extending outside of said enclosure; elongated pouch means attaced to the outside of one of said oppositely facing walls for removably receiving a surgical tool; and,
   a surgical tool overlying at least one of said electrodes and adapted to transmit force applied from it to said associated electrode whereby application of said force by said tool against a surface of a patient initially causes said electrodes to contact each other and to remain in contact until the entire surfaces of the electrodes are separated so as to indicate the maximum pressure to which any part of the electrode is exposed whereupon electrode contact is broken.

2. The surgical tool assembly of claim 1 wherein said enclosure is a flexible housing adapted to expand when the volume inside said enclosure increases due to a pressure increase.

3. The surgical tool assembly of claim 2 wherein said tool includes a substantially flat retractor blade for transmitting said force, said blade overlying said associated electrode, and a handle attached to said blade, said handle extending beyond said enclosure to facilitate usage of the tool assembly by an operator.

4. The surgical tool assembly of claim 3 wherein said blade and said underlying electrode are substantially equivalent in surface to surface area so that the force from said blade may be transmitted to said underlying electrode from any point along the length of said blade.

5. The surgical tool assembly of claim 3 wherein said blade area significantly exceeds the mating surface area of said underlying electrode and said assembly further includes a fluid-filling pocket overlying the other of said electrodes so that said housing containing said electrodes is sandwiched between said pouch and fluid-filled pocket whereby force from said blade may be transmitted to underlying electrode from any point along the length of said blade.

6. The surgical tool of claim 2 wherein said electrodes are attached to the interior surface of opposite, facing walls of said housing with said walls being movable away from each other under an increase of fluid pressure inside said enclosure.

7. The surgical tool assembly of claim 6 wherein said housing and said electrodes are rectangularly shaped with each electrode covering a major portion of the respective wall to which each is attached.

8. The surgical tool assembly of claim 1 wherein said electrodes are flexible and are adapted to contact each other over less than their entire surface area in response to local force applications by said tool.

9. The surgical tool assembly of claim 1 wherein said means for providing fluid flow into said enclosure includes a length of flexible tubing attached to said enclosure, said tubing adapted to be connected at its remote end to a fluid source for supplying fluid to said enclosure, said tubing also serving to enclose said electrical leads from said electrodes so that an electrical connection can be made at the remote end of said tubing.

10. A pressure-responsive device for use with a surgical tool comprising:
    an elongated inflatable enclosure having oppositely facing walls and having a distal end and a proximal end;

a pair of thin electrode strips positioned within said enclosure, said strips adapted to contact each other and operatively move away from each other under an increase in fluid pressure inside the enclosure until electrical contact is broken;

an electrical lead connected to each electrode;

means near the proximal end of said enclosure for providing fluid flow into said enclosure;

and elongated pouch means attached to the outside of one of said oppositely facing walls for removably receiving a surgical tool which is adapted to overlie at least one of said electrodes and to transmit force applied from it to said associated electrode.

11. An pressure-responsive retraction tool assembly comprising: an inflatable, flexible housing having opposite facing walls; a pair of thin, flexible electrode strips in said housing, each electrode strip attached to the interior surface of said opposite, facing walls of said housing, said housing and said electrode strips being substantially rectangularly shaped with each electrode strip covering a major portion o the respective facing wall to which each is attached, said electrode strips adapted to contact each other and operatively move away from each other under an increase of fluid pressure inside said housing until electrical contact is broken; a length of flexible tubing have a connection end and a remote end, said connection end attached to said housing and said remote end adapted to be connected to a fluid source for supplying fluid to said housing; an electrical lead connected to each electrode strip to provide an electrical connection therefor said leads extending out of said housing through said tubing and adapted to make an electrical connection at the remote end of said tubing; a pouch fixed to the outside of one of said oppositely facing walls and having a closed distal end and an open proximal end, a surgical retraction tool including a substantially flat and rectangular retraction blade overlying one of said electrode strips and being slidably removably retained in position inside said pouch, said blade adapted to transmit force applied from it to said associated electrode strip, said tool further including a handle attached to said blade for facilitating use of said tool assembly.

* * * * *